United States Patent [19]

Kaufman

[11] Patent Number: 5,053,546
[45] Date of Patent: Oct. 1, 1991

[54] CHIRAL COMPOUNDS OF THE BETA-BINAPHTHYL TYPE, THEIR PREPARATION AND THEIR USE

[75] Inventor: Dieter Kaufman, Bergisch Gladbach, Fed. Rep. of Germany

[73] Assignee: Bayer Aktiengesellschaft, Leverkusen, Fed. Rep. of Germany

[21] Appl. No.: 446,843

[22] Filed: Dec. 6, 1989

[30] Foreign Application Priority Data

Dec. 17, 1988 [DE] Fed. Rep. of Germany ....... 3842554

[51] Int. Cl.$^5$ ................................................ C07F 5/02
[52] U.S. Cl. ........................................... 568/4; 568/1; 568/6
[58] Field of Search ................... 568/1, 4, 6; 260/448 AD

[56] References Cited

U.S. PATENT DOCUMENTS

| | | | |
|---|---|---|---|
| 3,230,262 | 1/1966 | Köster | 568/1 |
| 4,284,581 | 8/1981 | Noyori | 260/448 AD |
| 4,644,075 | 2/1987 | Masamune | 568/1 X |
| 4,713,380 | 12/1987 | Brown | 568/1 |
| 4,772,752 | 9/1988 | Brown | 568/6 |

FOREIGN PATENT DOCUMENTS 2940336 4/1980 Fed. Rep. of Germany .

OTHER PUBLICATIONS

Chemical Abstracts vol. 108, Jan. 1988, Asymmetric reduction of prochiral arylketones with chiral 2,2'-dihydroxy-1,1'-binaphthylborane complexes p. 533.
Journal of Organometallic Chemistry vol. 344, 1988, Erste asymmetrische Synthese beta-binaphthylgestutzter Silane, Stannane und Borane pp. 277-283 U. M. Gross et al.
Tetrahedron Letters vol. 29, 1988, Chirality transfer from silicon to carbon: use of optically pure cyclic silanes with a binaphthalene chiral unit pp. 6199-6202.

*Primary Examiner*—Arthur C. Prescott
*Attorney, Agent, or Firm*—Sprung Horn Kramer & Woods

[57] ABSTRACT

New chiral compounds of the formula

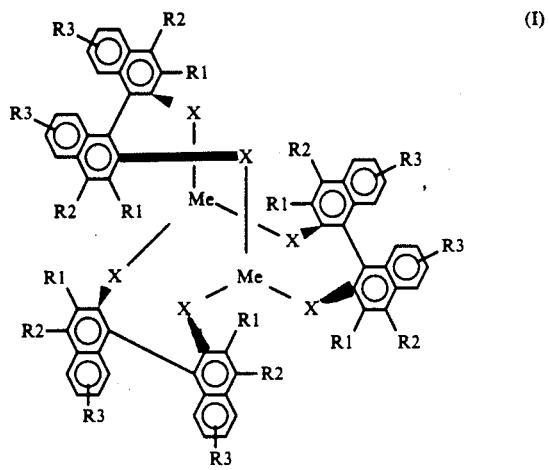

a process for their preparation and their use for the preparation of optically active compounds.

10 Claims, No Drawings

CHIRAL COMPOUNDS OF THE BETA-BINAPHTHYL TYPE, THEIR PREPARATION AND THEIR USE

The present invention relates to new chiral compounds of the β-binaphthyl type of the formula (I)

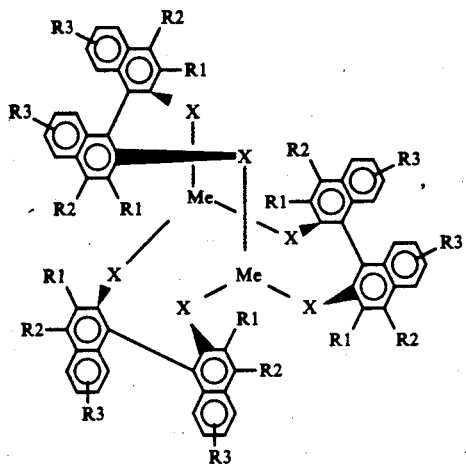

in which
Me represents B, Al, $CR^4$, $SiR^4$, $Sn(IV)R^4$, P or P=O where $R^4$ is hydrogen, $C_1$-$C_6$-alkyl, halogen, phenyl or O—$C_1$-$C_6$-alkyl,
X represents O, S or $NR^5$ where $R^5$ is hydrogen, $C_1$-$C_6$-alkyl or phenyl,
$R^1$ represents hydrogen, $C_1$-$C_6$-alkyl, tri-$C_1$-$C_4$-alkyl-silyl or substituted or unsubstituted, phenyl,
$R^2$ and $R^3$ can be identical or different and each represent hydrogen, $C_1$-$C_6$-alkyl, substituted or unsubstituted phenyl, tri-$C_1$-$C_4$-alkylsilyl, halogen or O—$C_1$-$C_6$—alkyl.

If $R^2$, $R^3$ and $R^4$ denote halogen, fluorine, chlorine and bromine, in particular fluorine and chlorine, are preferred. If $R^1$, $R^2$ and $R^3$ denote substituted or unsubstituted phenyl, examples of suitable substituents are $C_1$-$C_6$-alkyl, halogen or O—$C_1$-$C_6$-alkyl radicals.

Preference is given to compounds of the formula (I) in which
Me represents B, Al, $CR^4$ or P,
X represents O or S,
$R^1$ represents hydrogen, $C_1$-$C_4$-alkyl, tri-$C_1$-$C_2$-alkyl-silyl or phenyl and
$R^2$ and $R^3$ represent hydrogen.

Particular preference is given to the compound of the formula (I) in which Me represents B, X represents O and $R^1$ to $R^3$ represent hydrogen.

Further examples of suitable individual compounds of the formula (I) are those in which X is O, $R^2$ is hydrogen and $R^3$ is hydrogen and which have the following further substituents:

| Me | $R^1$ | $R^4$ |
|---|---|---|
| B | $CH_3$ | — |
|   | $C_2H_5$ | |
|   | $C_3H_7$ | |
|   | $C_6H_5$ | |
| Al | H | — |
| $CR^4$ | H | H |
|   |   | $CH_3$ |
|   |   | $C_2H_5$ |
|   |   | $C_6H_5$ |

| Me | $R^1$ | $R^4$ |
|---|---|---|
| | | F |
| | | Cl |
| | | $OCH_3$ |
| | | $OC_2H_5$ |
| $SiR^4$ | H | H |
| | | $CH_3$ |
| | | $C_2H_5$ |
| | | $C_6H_5$ |
| | | F |
| | | Cl |
| | | $OCH_3$ |
| | | $OC_2H_5$ |
| $SnR^4$ | H | H |
| | | $CH_3$ |
| | | $C_2H_5$ |
| | | $C_6H_5$ |
| | | F |
| | | Cl |
| | | $OCH_3$ |
| | | $OC_2H_5$ |
| P | H | — |
| P = O | H | — |

The present invention also relates to a process for the preparation of chiral compounds of the β-binaphthyl type of the formula (I), which is characterized in that a β-binaphthyl compound of the formula (II)

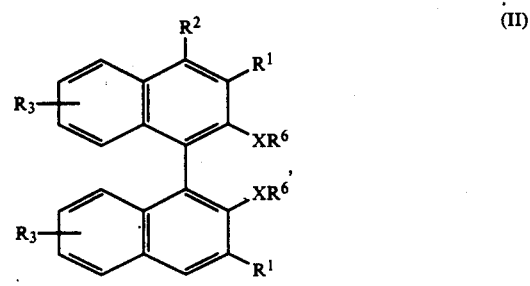

in which
X, $R^1$, and $R^3$ have the meaning mentioned in formula (I) and
$R^6$ represents hydrogen, $C_1$-$C_6$-alkyl or tri-$C_1$-$C_4$-alkyl-silyl with a compound of the formula (III)

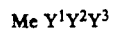 $Y^1Y^2Y^3$ (III), in which
Me has the meaning mentioned in formula (I) and
$Y^1$, $Y^2$ and $Y^3$ are identical or different and each represent hydrogen, fluorine, chlorine, bromine, iodine, $NH_2$, mono-$C_1$-$C_6$-alkyl-amino di-$C_1$-$C_6$-alkyl-amino, $C_6$-$C_{10}$-aryl-$C_1$-$C_6$-alkyl-amino, di-$C_6$-$C_{10}$-aryl-amino, OH, $C_1$-$C_6$-alkoxy, $C_6$-$C_{10}$-aryloxy, tri-$C_1$-$C_4$-alkyl-siloxy, $C_1$-$C_6$-thioalkoxy, $C_6$-$C_{10}$-thioaryloxy, $C_1$-$C_6$-alkyl or $C_6$-$C_{10}$-aryl.

If appropriate, the compounds of the formula (III) can be used in the form of adducts, for example boron compounds as etherates or thioetherates, such as $BF_3$ x $O(C_2H_5)_2$, $BH_3$ x tetrahydrofuran, $H_2B$ Cl x $O(C_2H_5)_2$ or $H_2BBr$ x $S(CH_3)_2$.

Inasfar as in formulae (II) and (III) symbols are used which are identical to those of formula (I), in formulae (II) and (III) those meanings which have been mentioned as preferred in formula (I) are also preferred. In formula (II), $R^6$ preferably represents hydrogen or trimethylsilyl; in formula (III), $Y^1$, $Y^2$ and $Y^3$, independently of one another, preferably represent hydrogen, chlorine, bromine, OH, methoxy and/or ethoxy.

Particularly preferred compounds of the formula (II) are β-binaphthol, β-thiobinaphthol, 2,2'-diamino-1,1'-binaphthyl and derivatives thereof which are substituted in the 3- and 3'-position by hydrogen, methyl, ethyl, propyl or phenyl.

Particularly preferred compounds of the formula (III) are boron trifluoride diethyl etherate, boron trichloride, $BH_3$ x tetrahydrofuran, chlorodihydroborane diethyl etherate and bromodihydroborane dimethyl sulfide.

The compounds of the formula (II) and (III) are either known or accessible in a manner analogous to that of the known compounds.

In a particular embodiment of the process according to the invention, the reaction is carried out in the presence of acid acceptors. Suitable acid acceptors are, for example, basic nitrogen compounds such as trialkylamines, dialkylcycloalkylamines, dialkylaralkylamines and dialkylarylamines. Preference is given to triethylamine, tripropylamine, tributylamine, dimethylcyclopentylamine, dimethylcyclohexylamine, diethylcyclopentylamine, diethylcyclohexylamine, dimethylbenzylamine, diethylbenzylamine and dimethylaniline.

If the reaction is to be carried out in the presence of acid acceptors, these can be used, for example, in amounts of 1 to 10 mol, relative to 1 mol of the compound of the formula (III).

The process according to the invention can be carried out in the presence or absence of diluents. Suitable diluents are inert or largely inert organic solvents which are liquid under the reaction conditions used in each case. Examples of these are aliphatic and aromatic hydrocarbons, halogenated hydrocarbons, ethers, ketones, esters, nitriles, amides, dimethyl sulfoxide and tetramethylene sulfone. Individual compounds are: pentane, hexane, heptane, octane, cyclohexane, methylcyclohexane, petroleum ether, benzine, ligroin, benzene, toluene, xylene, tetralin, methylene chloride, ethylene chloride, trichloroethylene, chloroform, carbon tetrachloride, chlorobenzene, dichlorobenzene, diethyl ether, dipropyl ether, diisopropyl ether, dibutyl ether, methyl tert.-butyl ether, glycol dimethyl ether, diglycol dimethyl ether, tetrahydrofuran, dioxane, acetone, methyl ethyl ketone, diethyl ketone, methyl isopropyl ketone, methyl isobutyl ketone, methyl tert.-butyl ketone, methyl acetate, ethyl acetate, propyl acetate, butyl acetate, amyl acetate, dimethyl phthalate, diethyl phthalate, acetonitrile, propionitrile, dimethylformamide, dimethyl acetamide and N-methylpyrrolidone. Methylene chloride, chloroform, chlorobenzene and dichlorobenzene are particularly preferred.

Suitable reaction temperatures for the process according to the invention are, for example, those between $-100°$ and $+250°$ C. Preferably, the process is carried out at $-40°$ to $+150°$ C.

For example, 0.6 to 7 mol of a compound of the formula (III) can be used, relative to 1 mol of a compound of the formula (II). Preferably, this ratio is 1:0.7 to 2.0, in particular 1:0.8 to 1.2.

In general, the reaction is carried out at atmospheric pressure. However, it is also possible to carry it out at reduced pressure or elevated pressure and use, for example, pressures in the range of 0.1 to 10 bar. It is often advantageous to work under an inert gas atmosphere, for example nitrogen.

In a particular embodiment of the process according to the invention, a solution of the compound of the formula (III) is added dropwise to a solution of the compound of the formula (II), and the reaction mixture is then stirred, for example, for 1 to 5 hours.

The work up of the reaction mixture is often very simple. For example, all volatile components can be removed in vacuo, which then gives a compound of the formula (I) as a solid residue which, if necessary, can be recrystallized, for example, from methylene chloride.

It is often possible to obtain the compounds of the formula (I) in the manner described above in yields of more than 90% of theory.

By means of the process according to the invention, the preparation of compounds of the formula (I) can be achieved in a simple manner, in a one-step process and in good to very good yields.

The present invention furthermore relates to the use of compounds of the formula (I) for the preparation of optically active compounds in concentrated or pure form. Examples of reactions in which by means of the compounds of the formula (I) as catalyst optically active compounds can be obtained in concentrated or pure form are asymmetric cycloaddition reactions, such as Diels-Alder reactions, asymmetric photo reactions, asymmetric catalytic hydrogenations (in this case the compounds of the formula (I) serve as ligands for catalytically active transition metal complexes) and asymmetric epoxidations. Examples of reactions in which by means of molar amounts of the compounds of the formula (I) optically active compounds can be obtained in concentrated or pure form are asymmetric ring openings of epoxides, asymmetric reductions of carbonyl and heterocarbonyl compounds, asymmetric hydrometalations, and asymmetric protonations.

In these reactions, it is a particular advantage that the compound of the formula (I) or (II) used can be recovered almost quantitatively after these catalytic reactions, for example by hydrolysis, without racemisation taking place.

EXAMPLES

Example 1

154.9 mg (1.0 mmol) of monobromoborane dimethyl sulfide were injected dropwise under nitrogen and at $-20°$ C. into a solution of 286.3 mg (1.0 mmol) of (S)-$(-)$-2,2'-dihydroxy-1,1'-binaphthyl. The mixture was then allowed to warm slowly to room temperature. All volatile components were then evaporated in vacuo and condensed. The remaining residue was dried at 50° C. and 0.1 mbar. This gave 282.8 mg (=97% of theory) of $(-)$-hexanaphtho[2,1-c:140 ,2'-e:2'',1''-j:1''',2'''-1:2'''',1''''-q:1''''',2'''''-s]-2,7,9,14,15,20-hexaoxa-1,8-diborabicyclo[6.6.6]eicosa-3,5,10,12,16,18-hexaene, m.p. >350° C. $^1$H-NMR (400 MHz, CDCl$_3$, J in Hz):δ=6.64 and 6.68 (AB system, $^3J$ =8.8, 4H), 7.06 (d, $^3J$=8.3, 2H), 7.22 (ddd, $^3J$=8.3, 6.7, $^4J$=1.3, 2H), 7.47 (ddd, $^3J$=8.1, 6.7, $^4J$=1.1, 2H), 7.74 (d, $^3J$=8.1, 2H), —MS (70 eV) m/z 877 (3%), 876 (22%), 875 (39%), 874 (11%).

X-ray structure analysis: $p\bar{1}$, a=9.3537 (10), b=14.4558 (13), c=19.1677 (19) Å, α=111.931(7), β=91.371 (8), =100.487(8)°, V=2352.2 (4) Å$^3$, Z=2 $d_{dcalc.}$=1.335 gcm$^{-3}$; Mo$_{K\alpha}$radiation (graphite monochromator); scan range $3° \leq 2\theta \leq 50°$; total number of reflections: 8272, observed reflections: 5749 ($F_o \geq 4\sigma(F)$), R=0.0526, R$_w$=0.0612. Nicolet R3m/V X-ray four-circle diffractometer, data calculated by SHELXTL-PLUS on MicroVAX II.

Average values of important bond length (Å) and angles (°) in the inner bicyclic region of the molecule, the standard deviations of the B—O and O—C bonds are 0.004 Å at most, and those of the C—C bonds 0.006 Å at most.

B—O 1.358; O—C 1.392; C—C linkage of the naphthyl groups 1.495; C(O)—C (linked) 1.367; C(O)—C (not linked) 1.406; C—C (central bond of the naphthyl groups) 1.419; B—B 3.397;O—B—O 120.0; B—O—C 124.9; O—C—C (linked) 116.8; torsional angle C(O)—C (linked)—C (linked)—C(O) 80.

Example 2

282.6 mg (0.32 mmol) of the compound obtained according to Example 1 were dissolved in 25 ml of dry dichloromethane, and at −78° C. under nitrogen first 736 mg (10.5 mmol) of methacrolein and after 15 minutes 661 mg (10.0 mmol) of cyclopentadiene were injected dropwise. The reaction mixture was kept at −78° C. for 2 days and then allowed to warm slowly to 0° C. It was then extracted twice with 10 ml each of saturated sodium bicarbonate solution, all volatile components were evaporated at room temperature in vacuo, and the product was then distilled at 50° C. and 0.01 torr. The yield was 1.16 g (85% of theory) of a mixture of 97.4 % by weight of (+)−exo- and 2.6% by weight of endo-2-methylbicyclo[2.2.1]heptene-2-carboxaldehyde. The enantiomeric excess of the exo product, determined by $^1$H-NMR spectroscopy after addition of tris[3-(heptafluoropropylhydroxymethylene)-d-camphorato]europium by integration of the aldehyde proton resonances, was 90%.

What is claimed is:

1. Chiral compounds of the B-naphthyl type of the formula (I)

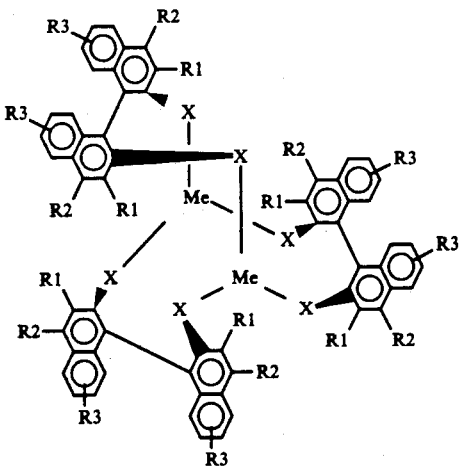

in which
 Me represents B
 X represents O, S or NR$^5$ where R$^5$ is hydrogen, C$_1$-C$_6$-alkyl or phenyl,
 R$^1$ represents hydrogen, C$_1$-C$_6$-alkyl, tri-C$_1$-C$_4$-alkylsilyl or substituted or unsubstituted phenyl,
 R$^2$ and R$^3$ can be identical or different and each represent hydrogen, C$_1$-C$_6$-alkyl, substituted or unsubstituted phenyl, tri-C$_1$-C$_4$-alkylsilyl, halogen or O—C$_1$-C$_6$-alkyl.

2. Chiral compounds according to claim 1, characterized in that
 Me represents B
 X represents O or S,
 R$^1$ represents hydrogen, C$_1$-C$_4$-alkyl or tri-C$_1$-C$_2$-alkylsilyl or phenyl and
 R$^2$ and R$^3$ represent hydrogen.

3. Chiral compound of claim 1 in which
 Me represents B,
 X represents O and
 R$^1$ and R$^3$ represent hydrogen.

4. A process for the preparation of chiral compounds of the formula (I)

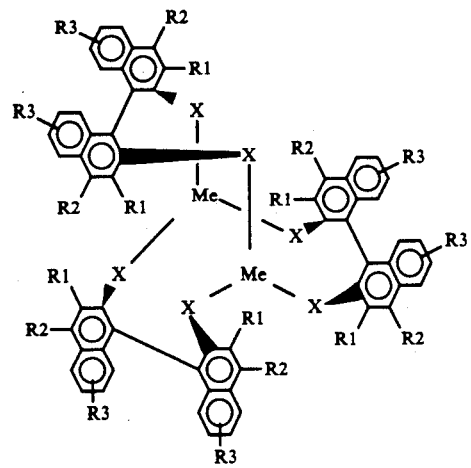

in which
 Me represents B
 X represents O, S or NR$^5$ where R$^5$ is hydrogen, C$_1$-C$_6$-alkyl or phenyl,
 R$^1$ represents hydrogen, C$_1$-C$_6$-alkyl, tri-C$_1$-C$_4$-alkylsilyl or substituted or unsubstituted phenyl,
 R$^2$ and R$^3$ can be identical or different and each represent hydrogen, C$_1$-C$_6$-alkyl, substituted or unsubstituted phenyl, tri-C$_1$-C$_4$-alkylsilyl, halogen or O—C$_1$-C$_6$-alkyl which is characterized in that a B-binaphthyl compound of the formula (II)

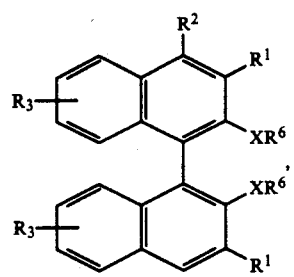

in which
 X, R$^1$, R$^2$ and R$^3$ have the meaning mentioned in formula (I) and
 R$^6$ represents hydrogen, C$_1$-C$_6$-alkyl or tri-C$_1$-C$_4$-alkyl-silyl is reacted with a compound of the formula (III)

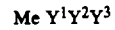

in which
 Me has the meaning mentioned in formula (I) and $Y^1$, $Y^2$ and $Y^3$ are identical or different and each represent hydrogen, fluorine, chlorine, bromine, iodine, $NH_2$, mono-$C_1$–$C_6$-alkyl-amino, di-$C_1$–$C_6$-alkyl-amino, $C_6$–$C_{10}$-aryl-$C_1$–$C_6$-alkyl-amino, di-$C_6$–$C_{10}$-aryl-amino, OH, $C_1$–$C_6$-alkoxy, $C_6$–$C_{10}$-aryloxy, tri-$C_1$–$C_4$-alkyl-siloxy, $C_1$–$C_6$-thioalkoxy, $C_6$–$C_{10}$-thioaryloxy, $C_1$–$C_6$-alkyl or $C_6$–$C_{10}$-aryl.

5. The process of claim 4, in which the compounds of the formula (III) are used in the form of adducts.

6. The process of claim 4 which is carried out in the presence of acid acceptors.

7. The process of claim 4 which is carried out at $-100°$ to $+250°$ C.

8. The process of claim 4, in which 0.6 to 7 mol of a compound of the formula (III) are used, relative to 1 mol of a compound of the formula (II).

9. The method of using the compounds of claim 1 for the preparation of optically active compounds in concentrated form.

10. The method of using the compounds of claim 1 for the preparation of optically active compounds in pure form.

* * * * *